United States Patent [19]

Battagin et al.

[11] Patent Number: 4,592,236

[45] Date of Patent: Jun. 3, 1986

[54] CONTAINER MONITORING SYSTEM USING ULTRASONIC SEALS

[75] Inventors: Gianpietro Battagin, Angera; René Denis, Laveno; Guilio Ghiringhelli, Angera, all of Italy; Alain Beaubron; Phillippe Guay, both of Dijon; Alfred Schaal, Massy, all of France

[73] Assignees: Communate Europeenne de l'Energie Atomique (Euratom), Luxembourg, Luxembourg; Commissariat a l'Energie Atomique, Paris, France

[21] Appl. No.: 450,013

[22] Filed: Dec. 15, 1982

[30] Foreign Application Priority Data

Dec. 22, 1981 [FR] France ................................ 81 23997

[51] Int. Cl.$^4$ ............................................. G01N 29/04
[52] U.S. Cl. ......................................... 73/602; 340/572
[58] Field of Search ....................... 340/518, 568, 572; 73/597, 599, 602, 624; 367/93; 376/249

[56] References Cited

U.S. PATENT DOCUMENTS

| | | | |
|---|---|---|---|
| 4,088,028 | 5/1978 | Hildebrandt | 73/624 X |
| 4,126,514 | 11/1978 | Wonn | 376/252 |
| 4,359,903 | 11/1982 | Crutzen et al. | 73/602 |
| 4,384,489 | 5/1983 | Crutzen et al. | 73/602 |

FOREIGN PATENT DOCUMENTS

| | | |
|---|---|---|
| 0018198 | 10/1980 | European Pat. Off. |
| 0018215 | 10/1980 | European Pat. Off. |
| 2311300 | 12/1976 | France |
| 2358702 | 2/1978 | France |

OTHER PUBLICATIONS

"Component Identification Using Ultrasonic Signature Analysis", *Materials Evaluation*, by J. L. Rose et al., Mar. 1983, pp. 315–318.
International Atomic Energy Agency (IAEA), "Application of Tamper-Resistant Identification and Sealing Techniques for Safeguards", *Safeguarding Nuclear Materials*, vol. II, 1976, IAEA, Vienna Austria, pp. 305–338, Crutzen et al.

*Primary Examiner*—James L. Rowland
*Assistant Examiner*—Brian R. Tumm
*Attorney, Agent, or Firm*—Dennis P. Clarke

[57] ABSTRACT

System for monitoring a plurality of containers using ultrasonic seals integral with the containers and electronic circuits connected to these seals, wherein:

(A) each seal comprises an ultrasonic transmitting transducer and an ultrasonic receiving transducer making it possible to check both the identity of the marking and the integrity of the seal, the marking being located outside the seal body, (B) the electronic circuits connected to these seals comprise:
 (a) at least one cyclic, sequential module for the auscultation or listening to the seals having the same number of outputs and inputs as there are seals, the outputs being connected to the transmitting transducers and the inputs to the receiving transducers,
 (b) at least one electronic processing module connected to the listening module and controlling a sampling of the signal received.

4 Claims, 11 Drawing Figures

CONTAINER MONITORING SYSTEM USING ULTRASONIC SEALS

BACKGROUND OF THE INVENTION

The present invention relates to a system for monitoring a plurality of containers using ultrasonic seals. It is used in the monitoring of a large number of containers containing dangerous products, precious materials, documents, etc.

The principle of monitoring by ultrasonic seals is known. It consists of definitively fixing an ultrasonic seal to the container to be monitored, said seal being provided with a unique marking, which is not reproducible located in the vicinity of the predetermined seal breaking area. This marking is obtained by structural irregularities of the matrix containing the seal, e.g. by material inclusions or cavities distributed in a random manner.

This serves the double function of checking the identity of the marking and checking the integrity of the seal. It involves a comparison between a test signal from the seal and a stored reference signal.

Generally an ultrasonic seal comprises a transducer able to convert an electrical excitation into an ultrasonic wave and vice versa. The structural irregularities present on the path of the transmitted ultrasonic wave give rise to ultrasonic echoes which are detected by the transducer, the latter supplying an electric signal, whose complex form is specific to the seal. There are electronic means for exciting the transducer, collecting the electric signal which it supplies and analyzing said signal.

In such a device, the ultrasonic transducer works both as a transmitter and as a receiver, in such a way that the seal only has a single transducer. However, British patent application No. 79 14 203 describes a marked seal, whose matrix contains two piezoelectric transducers. However, in such a seal, one of the transducers is used for detecting the identity of the marking and the other for checking the integrity of the seal. Thus, each of these transducers serves as a transmitter and as a receiver of the ultrasonic signals.

Such seals are unable to operate sufficiently accurately and rapidly to be used in large numbers.

BRIEF SUMMARY OF THE INVENTION

The present invention relates to a system which is especially adapted both from the mechanical and electronic standpoints to the monitoring of a large number of units (several hundred or several thousand).

Thus, the invention relates to a system, wherein:
(A) each seal comprises an ultrasonic transmitting transducer and an ultrasonic receiving transducer making it possible to check both the identity of the marking and the integrity of the seal, the marking being located outside the seal body,
(B) the electronic means connected to these seals comprise:
  (a) at least one cyclic, sequential module for the auscultation or listening to the seals having the same number of outputs and inputs as there are seals, the outputs being connected to the transmitting transducers and the inputs to the receiving transducers,
  (b) at least one electronic processing module connected to the listening module and controlling a sampling of the signal received.

If such a system is able to scan a large number of seals with a rapid cycle (less than 2 seconds) it is possible to work with a small number (a few units).

In connection with each seal, improvements are made, so that they have a better electrical performance, better signal discrimination power, whilst permitting the reuse thereof.

Essentially these improvements involve contacting the transducers with an element serving as a delay line for the ultrasonic signals; in the displacement of the identification marking outside the body of the seal into a mechanical element in the form of a stud or pin which carries the seal, anchoring the seal in the container sealing system and acoustic extension of the delay line; the symmetrical arrangement of the elements constituting the seal and positioning the actual seal around the axis of symmetry of the stud; finally the connection between the seal and the stud.

With respect to the electronic means, the invention provides a structure making it possible to very rapidly, cyclically and sequentially listen to seals, making it possible to monitor a large number thereof, which was not possible with the prior art electronic means. For example, the elementary module scans cyclically 16 seals in two seconds. The association of n identical modules permits the auscultation of 16 n seals in the same time of 2 seconds.

BRIEF DESCRIPTION OF THE DRAWINGS

The invention is described in greater detail hereinafter relative to non-limitative embodiments and with reference to the attached drawings, wherein show.

DETAILED DESCRIPTION OF THE PREFERRED EMBODIMENTS

Figure 1:
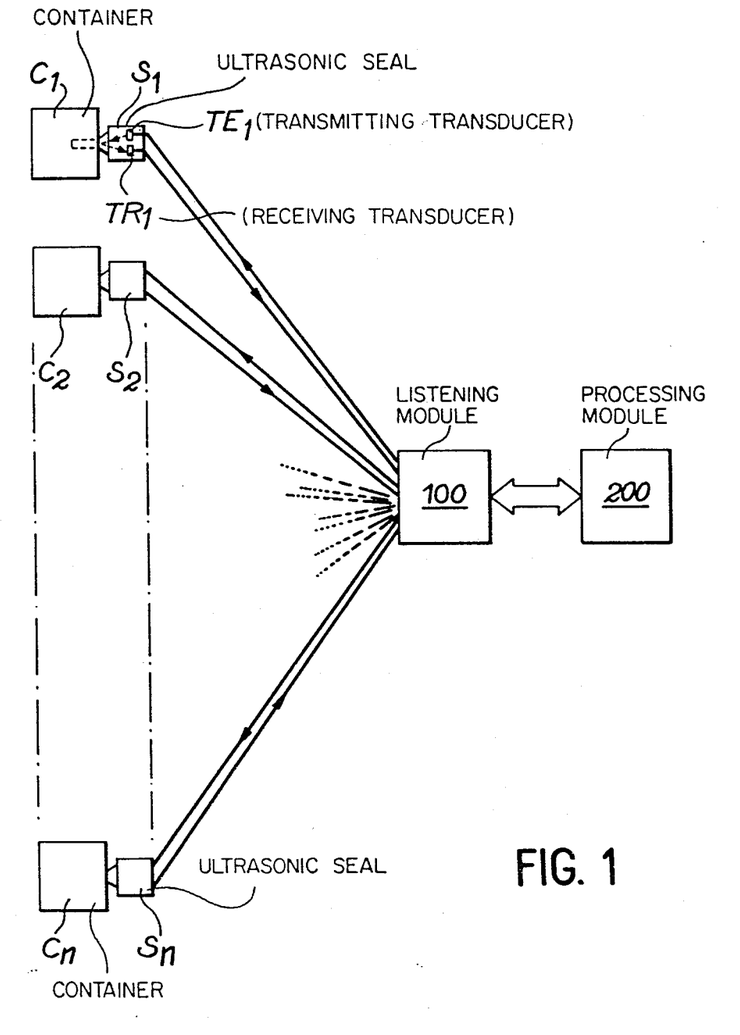
FIG. 1—the general diagram of the system according to the invention.

The system shown in FIG. 1 comprises a plurality of n containers $C_1, C_2 \ldots C_n$, each provided with an ultrasonic seal $S_1, S_2, \ldots S_n$. Each seal has a transmitting transducer $TE_1, TE_2 \ldots TE_n$ and a receiving transducer $TR_1, TR_2, \ldots TR_n$. These transducers are connected by the same number of double connections to a listening or auscultation module 100, the latter being controlled by a processing module 200.

Figure 2:
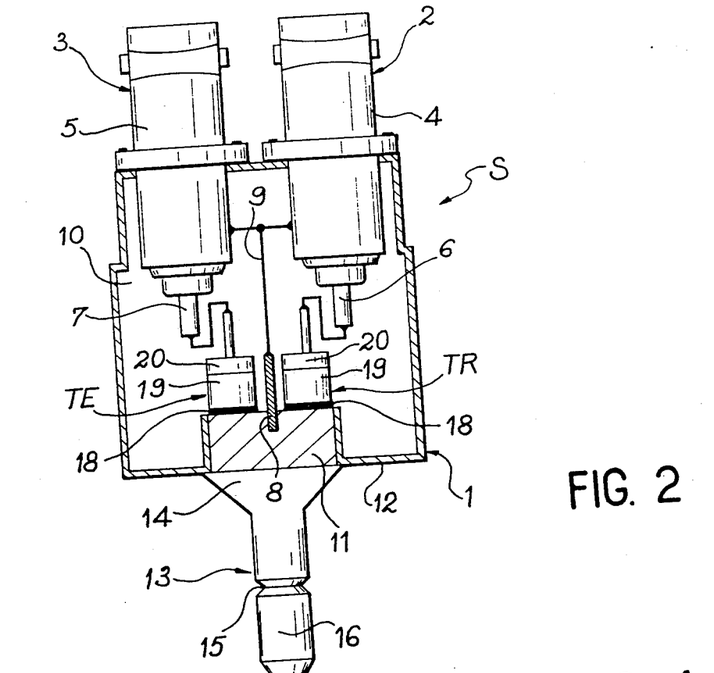
FIG. 2—is section an ultrasonic seal according to the invention.

A seal according to the invention is illustrated in detail in FIG. 2. The seal comprises a body 1 having in its upper part two coaxial connections 2,3 connected to the listening module, a transmitting transducer TE and a receiving transducer TR, both connected to the Cores 6 and 7 of the coaxial connections. A conductive plate 8 forming an electrical shield is interposed between the two transducers TE and TR. This plate is connected by wires 9 to the external conductors 4, 5 of connections 1, 2. Each transducer comprises a piezoelectric element 18, an electrically conductive damper 19 made from resin (e.g. epoxy resin) filled with metallic particles in a high concentration (tungsten) and a contact electrode 20. The transducers are glued to the delay line 11 by means of a cyaniacrylate glue.

The lower part of connections 2 and 3, transducers TE and TR and plate 8 are coated with an epoxy resin volume 10.

The piezoelectric parts 18 of transducers TE and TR are glued to an element 11 forming a delay line for the ultrasonic wave. This element can be made from DURALUMIN (aluminum alloy), its end being flushed with the surface 12 of the seal. A sealing stud or pin 13, e.g. of DURALUMIN (aluminum alloy), is glued to the surface 12 of the seal. It is therefore in contact with delay line 11. This stud has an acoustic identity.

Stud 13 is in three parts, a waveguide 14, a breaking area 15 and an anchoring area 16. The latter is inserted in the cover of the container to be monitored. The stud must necessarily be broken at the breaking area 15 to enable the container to be opened. The part which remains integral with the stud after breaking is removed by machining and the seal can be recovered, a new stud being fixed by gluing.

Artificial defects can be made on the surface of the stud to be glued to surface 12 and these defects are involved in the identity of the seal or the recovered seal.

The delay line 11 and stud 13 must be glued to one another. The glue coating thickness must permit a suitable acoustic matching. It is for example approximately 20 μm thick. It is possible to use a cyaniacrylate type glue, e.g. Eastman Kodak 910.

The ultrasonic transmitting transducer TE is excited by a high voltage electric pulse, e.g. of 200 v and with a rise time of 50 to 100 ns. The transducer produces an acoustic wave, which is propagated through the delay line, reaches surface 12 to which the stud is glued and is partly reflected by the defects present there. The wave reflected by these defects reaches the receiving transducer TR, which then supplies a low voltage signal. Its frequency is approximately 5 MHz and its peak value 100 mV, with a time lag of 5 μs and a duration of 10 μs. This signal constitutes the identity of the seal. It also contains integrity information, bearing in mind that any significant deterioration of the stud and in particular its breaking, has a very definite modifying action on the form of the signal.

Figure 3:
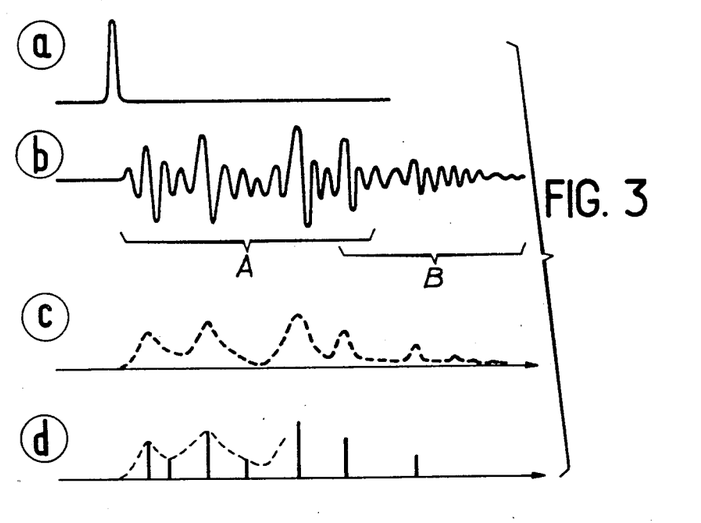
FIG. 3—the form of the signals used in the system according to the invention.

FIG. 3 shows the configuration of the signals involved in the invention. The electrical excitation pulse applied to transmitting transducer TE appears on line a and the reception signal supplied by transducer TR on line b. There is a delay between the two, which is due to delay line 11. Moreover, shielding 8 prevents any electrical interference on the reception signal at the time of excitation. Two areas can be distinguished in the reception signal, the first A, which is more particularly an identity area, and a second B, which partly coincides with the first and which is an integrity area because the signals forming it come from the areas most remote from the transducers, i.e. the stud. The reception signal is then rectified (line c) and then sampled (line d) by electronic means.

The system according to the invention, which therefore relates to the combination of the mechanical and electronic means, makes it possible to obtain signals leading to increased measuring speed and precision, compared with the prior art devices.

The following description relates to the electronic means able to listen to a plurality of seals, like that described hereinbefore. For purely explanatory purposes, it will be assumed that there are 16 sealed containers to be monitored. The various elements will therefore carry the subscripts 1 to 16, but larger numbers are also possible.

In a general manner, the electronic means according to the invention operate as follows. The seals are scanned sequentially and cyclically by module 100 under the control of processing module 200. The auscultation or listening module samples the signal for a certain number of values (e.g. 6), corresponding to particular sampling times (e.g. 4 values for part A of the signal corresponding to the identity information and two values for part B, corresponding to the integrity information). The values of the samples are then digitally converted and transmitted to processing module 200. The latter compares the values, after digital processing, with those in its memory, in order to deduce the identity therefrom and check the integrity of the seal in question. The processing module can also initiate special procedures (alarms, etc.) as a function of the results of the controls carried out.

This sequence of electronic processing operations is made possible by the special structure of the seal described hereinbefore and by the form of the signal to be processed. It is this cooperation between the means, which gives the system according to the invention its excellent precision and speed performances.

Figure 4:
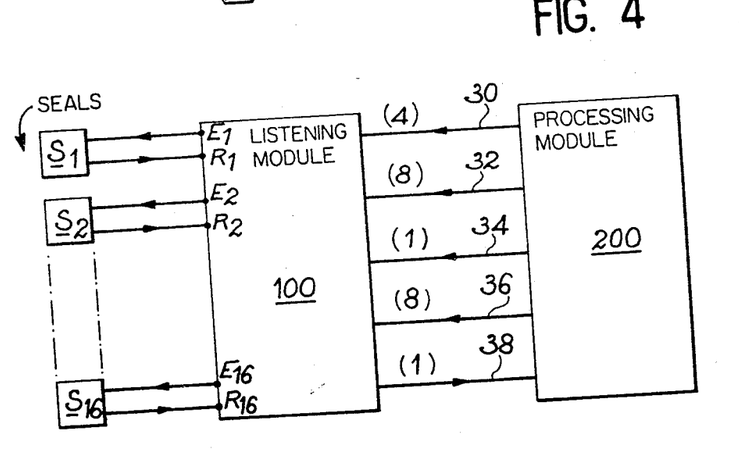
FIG. 4—the inputs - outputs of the seal listening module.

As indicated in FIG. 4, the seal listening module 100 comprises 16 accesses serving for transmission ($E_1$, $E_2$, ... $E_{16}$) and 16 accesses for reception ($R_1$, $R_2$ ... $R_{16}$). Each of these accesses is connected by a coaxial transmission cable and a coaxial reception cable to the receiving or transmitting transducers of the corresponding seal. In addition, module 100 is connected to the processing module 200 by a seal addressing bus having four bits and permitting the addressing of 16 seals; an 8 bit bus 32 carrying the signals determining the sampling times of the reception signals, said sampling times ranging between 0 and 25.5 μs in 0.1 μs steps; a connection 34 for initiating the measurement informing the modules for producing the seals to start the measurement for the seal and sample in question; an 8 bit data bus 36 carrying the values of the amplitude measured for the various samples, said values varying e.g. from 0 to 512 mV, to within 2 mV; a connection 38 carrying a signal indicating to the processing module 200 that the measurement performed by the seal listening module 100 has been completed and that the processing of the results can start.

Figure 5:
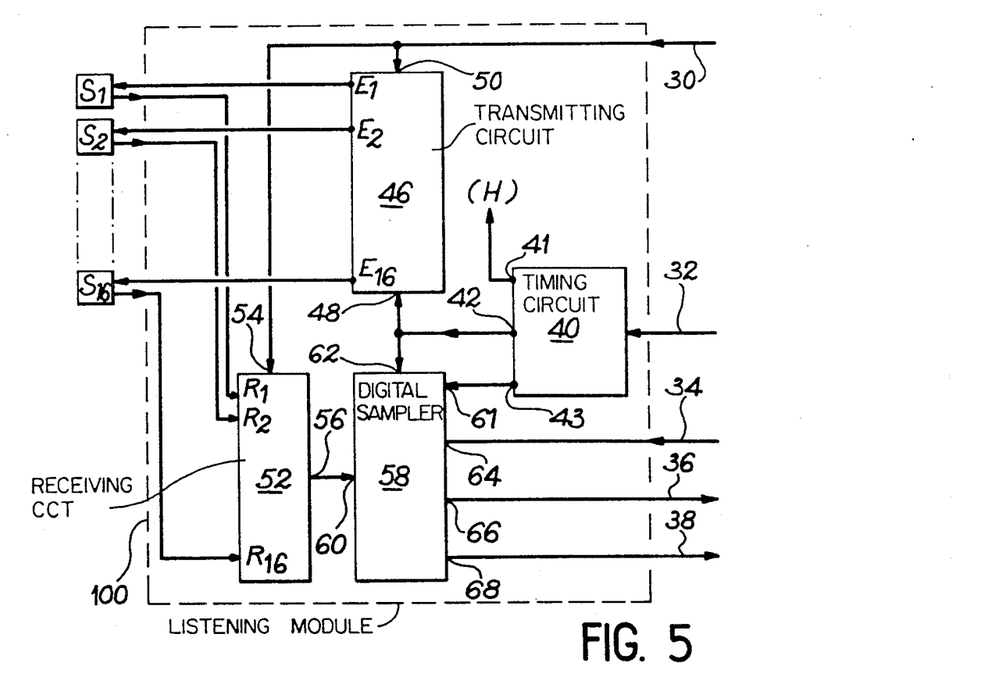
FIG. 5—the block diagram of this module.

The general organization of module 100 is shown in FIG. 5 and comprises four essential circuits:

a timing circuit 40 with three outputs 41, 42, 43, respectively supplying a timing pulse H, a synchronizing pulse and a delayed pulse, said circuit receiving the signal carried by connection 32;

a transmitting circuit 46 having the same number of transmitters and the same number of outputs $E_1$, $E_2$ etc. as there are seals to be checked (in the present case 16), each output being connected to the transmitting transducer of a seal, said circuit having an addressing input 50 connected to the addressing bus 30 carrying the addressing signal and a control input 48 connected to output 42 of timing circuit 40, said input receiving the synchronizing pulse;

a receiving circuit 52 having an addressing input 54 connected to the addressing bus 30, the same number of inputs $R_1$, $R_2$ etc. as there are seals to be checked, each input being connected to the receiving transducer of the associated seal, and an output 56;

a digital sampler 58 having a signal input 60 connected to the output 56 of receiving circuit 52, a first control input 61 connected to the output 43 of timing circuit 40 and receiving the delayed pulse determining the sampling time, a second control input 62 connected to the output 42 of the timing circuit and receiving the pulse controlling the measurement, a first output 66 connected to the pulse 36 carrying the digital value of a sample and a second output 68 connected to the connection 38 carrying the pulse indicating that sampling has been completed.

These various subassemblies are illustrated in greater detail in FIGS. 6 to 11, which will now be described.

Figure 6:
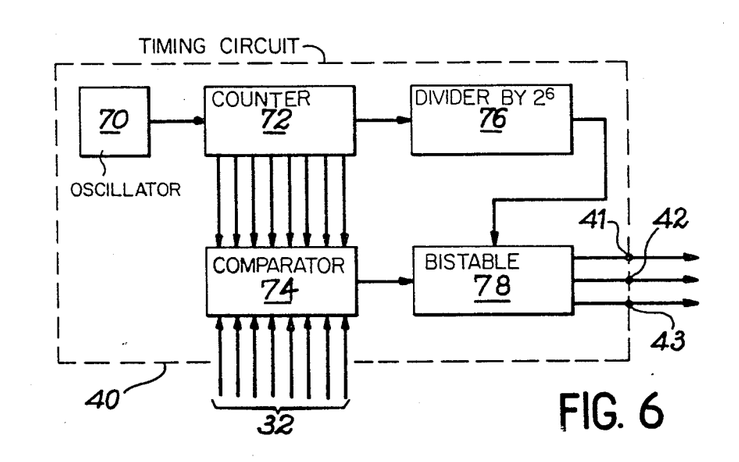
FIG. 6—a timing circuit.

Firstly FIG. 6 illustrates timing circuit 40, which comprises an oscillator 70 operating at 10 MHz and constructed e.g. with the aid of an integrated circuit SN 74 629 of Texas Instruments. The period of the pulses transmitted by this oscillator is 0.1 μs. These pulses are supplied to an 8 bit counter 72, constituted e.g. by two circuits SN 74 163 (capacity 256). At the output of the counter, the pulses have a period of 25.6 μs. An 8 bit comparator 74 constituted e.g. by 2 circuits SN 7485, compares the content of counter 72 with the number appearing on bus 32. Thus, at the output of the comparator, appears a pulse delayed by N times 0.1 μs, if N is the number present on bus 32. Counter 72 is followed by a divider by $2^6$, 76, constituted e.g. by two circuits SN 74 LS 163. Thus, the output of this divider supplies pulses with a period equal to $25.6 \times 2^6 \simeq 1.64$ ms. A bistable circuit 78, formed e.g. by a flip-flop SN 74 LS 72 and a double monostable SN 74 LS 123 shapes the preceding pulses. Thus, at outputs 41, 42, 43 of the timing circuit, there are then a timing pulse H, a synchronizing pulse and a delayed sampling pulse.

Figure 7:
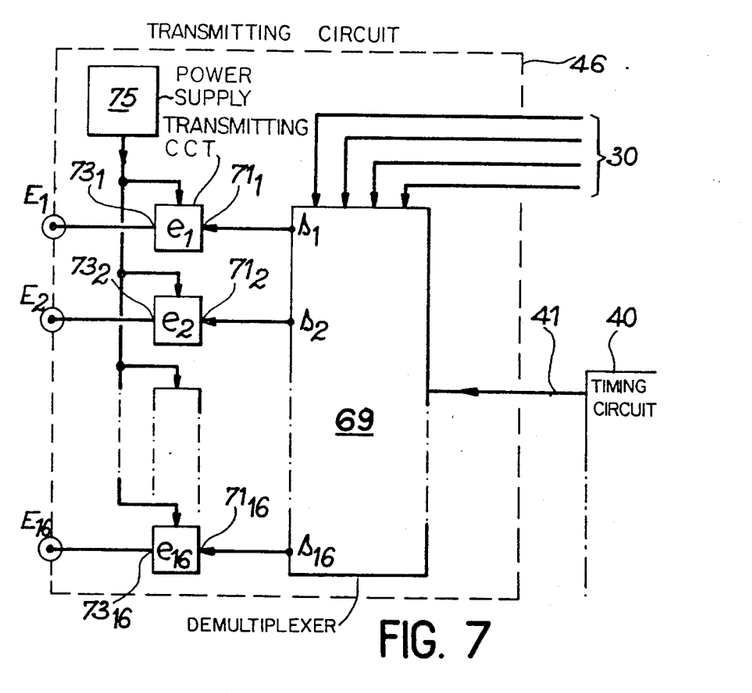
FIG. 7—a multiple transmitting circuit.

FIG. 7 shows the circuit diagram of transmitter 46, which comprises a demultiplexer 69 having an input connected to connection 41 receiving the timing pulse and the same number of outputs $s_1$, $s_2$, etc. as there are seals and a group of transmitting circuits $e_1$, $e_2$, etc. in the same number as there are seals, each transmitter having a control input $71_1$, $71_2$, etc. connected to an output of the demultiplexer and an output $73_1$, $73_2$, etc. connected to one of the outputs $E_1$, $E_2$, etc. of the transmitting circuit. Each transmitter is also connected to a power supply 75.

The demultiplexer can comprise an integrated circuit SN 74 LS 154. In the present embodiment it receives a four bit address and selects one output from among 16.

Figure 8:
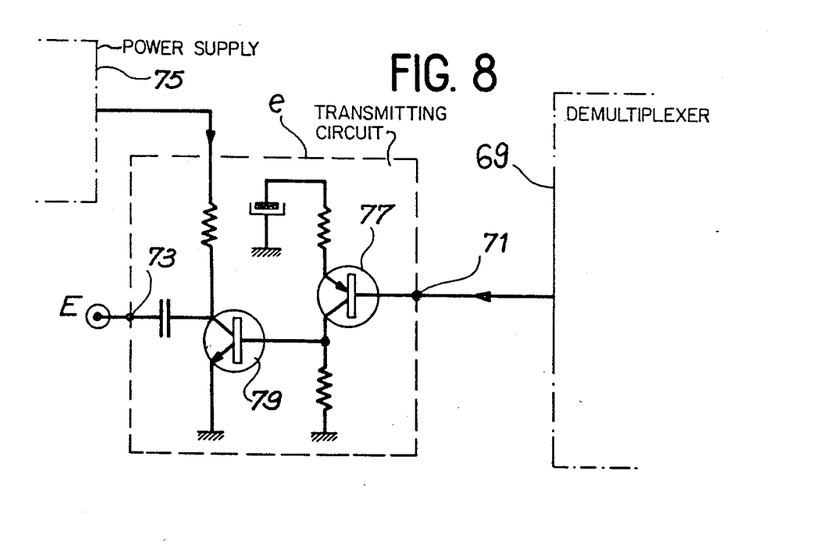
FIG. 8—an embodiment of a transmitter.

As indicated in FIG. 8, each transmitter can comprise a first transistor 77, whereof the base is connected to the input 71, connected to demultiplexer 70 and the collector to the base of a solid thyratron 79, whose grid is connected both to the power supply 75 and to the output 73. Transistor 77 can be a 2N 2907 and the solid thyratron 79 a 2N 1599. Power supply 75 can supply approximately 300 V. The transmitter supplies pulses of 200 V/50 ohm.

Figure 9:
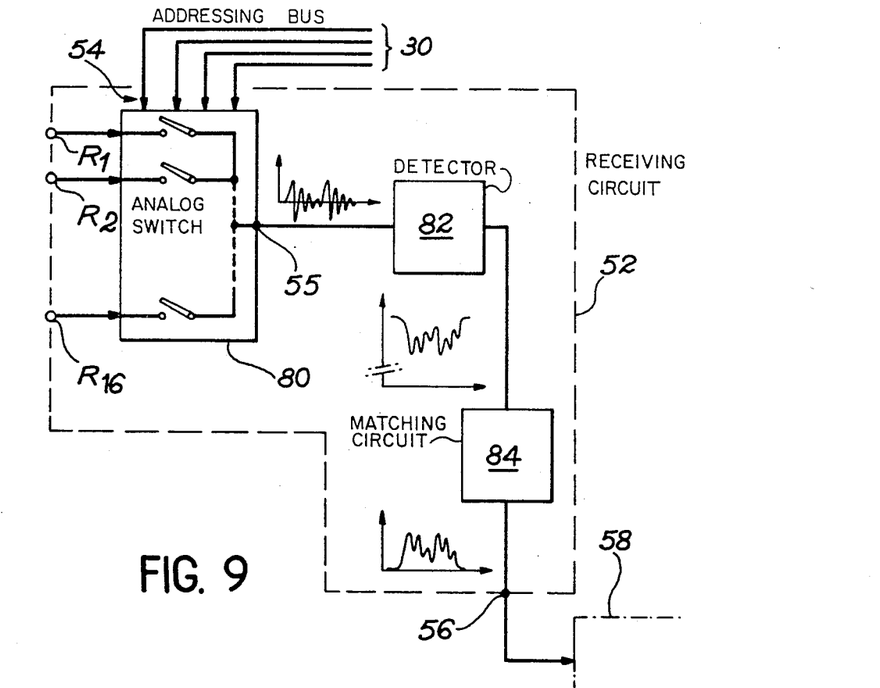
FIG. 9—a receiving circuit.

FIG. 9 is a block diagram of a receiving circuit 52 usable according to the invention. This circuit comprises an analog switch 80 (e.g. of type DG 506) having the same number of inputs $R_1$, $R_2$, etc. as there are seals, a control input 54 connected to addressing bus 30, an output 55 connected to a detector 82 constituted e.g. by an integrated circuit NC 1596. When the detected signal is superimposed at a continuous non-zero level (which is the case with the integrated circuit NC 1596), a matching circuit 84 is positioned at the output of the circuit.

Figure 10:
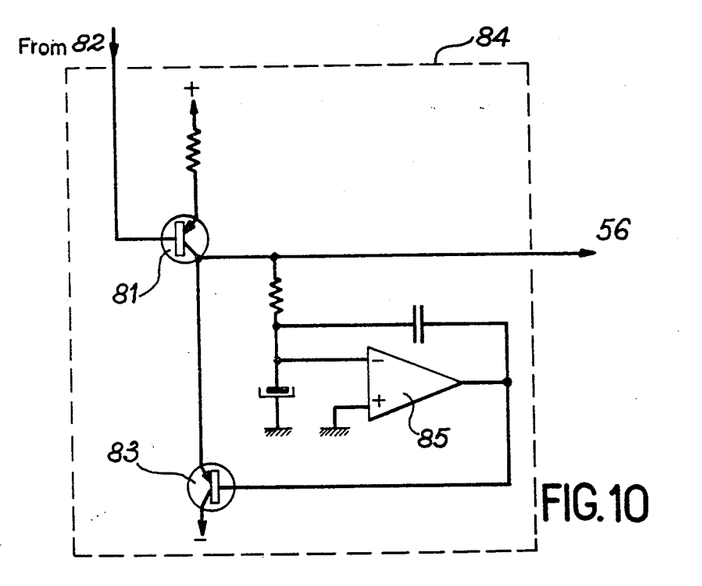
FIG. 10—a matching circuit.

As shown in FIG. 10, said matching circuit can be realized with the aid of two transistors 81, 85 (e.g. type 2N 2907) and an operational amplifier 85 (e.g. a SN 72 741) for transposing the detected signal above 0 V. In the present embodiment, the output signal lasts approximately 10 or 15 μs and has an amplitude between 200 and 500 mV.

Figure 11:
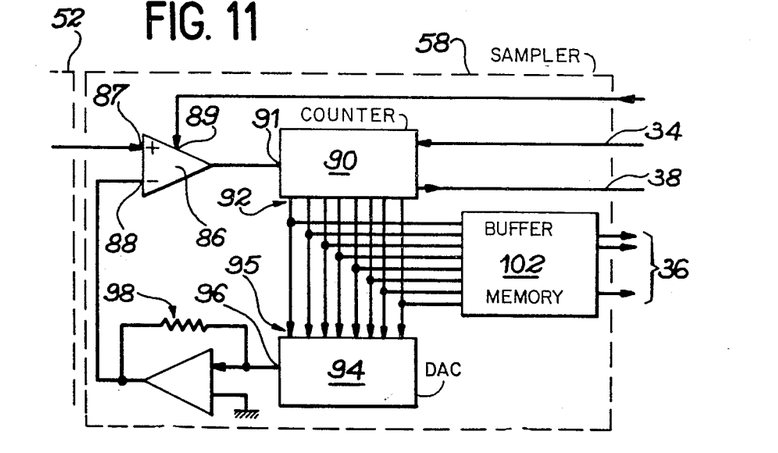
FIG. 11—an embodiment of a sampler.

Finally, FIG. 11 shows the diagram of sampler 58, which comprises:

- a rapid comparator 86, having a positive input 87 receiving the signal to be sampled, a negative input 88 and a sampling control input 89 which is of the locked type, whilst said comparator can be of type AM 686;
- a counter 90 having an input 91 connected to the output of the comparator and a digital output 92, whereby said counter can be a register operating on the :dichotomy principle, e.g. a MC 14559;
- a digital-analog converter 94 having a digital input 95 connected to the output 92 of the counter and an analog output 96, said converter can be a AD 561;
- a current-voltage converter 98 inserted between the output of the converter and the negative input 88 of the comparator, said converter can be a SN 72 740;
- a buffer memory 102 having an input connected to the output of the counter and an output connected to the data bus 36, said memory can be constituted by a circuit SN 7407 (8 bits).

This circuit functions in the following manner. The signal to be sampled is applied to the input 87 of comparator 86. The signal controlling the sampling is applied to input 89. If the signal to be sampled exceeds the voltage applied to input 88 at the time when the sampling signal is applied, the comparator output passes to level 1 and increments counter 90. The digital output of the counter is transformed into an analog value, which is used as a comparison voltage at the input 88 of the comparator. By successive approximations and at the end of 8 timing pulses, the content of the counter is equal to the input signal at the sampling time. The total time per sample is in practice 10 times 1.6 ms, i.e. 16 ms. Output 92 of the counter (8 wire bus) is connected to the buffer memory 102, which is of the open collector type. The latter supplies the digital value of the sample to output bus 36. A pulse is supplied by counter 90 via connection 38, when the measurement is ended.

What is claimed is:

1. A system for monitoring a plurality of containers using ultrasonic seals integral with said containers and electronic means connected to these seals, wherein:
   (A) each seal comprises an ultrasonic transmitting transducer and an ultrasonic receiving transducer making it possible to check both an acoustic identity of a marking and an integrity of the seal,
   (B) the electronic means connected to these seals comprise:
   (a) at least one cyclic, sequential module for the auscultation or listening to the seals having the same number of outputs and inputs as there are seals, the outputs being connected to the transmitting transducers and the inputs to the receiving transducers,
(b) at least one electronic processing module connected to the listening module and controlling a sampling of the signal received,
wherein the seal listening module comprises:
a timing circuit having three outputs respectively supplying a timing pulse, a synchronizing pulse and a delayed pulse;
a transmitting circuit having the same number of transmitters as there are seals to be checked, each transmitter being connected to the transmitting transducer of a seal, said circuit having an addressing input connected to an addressing bus from the processing module and carrying an addressing signal and a control input connected to the timing circuit and receiving the synchronizing pulse;
a receiving circuit having the same number of inputs as there are seals to be checked, each input being connected to the receiving transducer of a seal and an output supplying a detected signal;
a digital sampler having a signal input connected to the output of the receiving circuit and a first control input receiving the delayed pulse determining the sampling time, a second control input controlling a measurement, a first output connected to a bus carrying the digital value of the sample and a second output connected to a connection carrying a pulse, when sampling is ended.

2. A system according to claim 1, wherein the transmitting circuit comprises a demultiplexer having an input connected to the connection receiving the timing pulse and the same number of outputs as there are seals, said addressing input connected to the addressing bus, and a group of transmitting circuits, whose number is equal to the number of seals, each transmitter having a control input connected to an output of the demultiplexer and an output connected to one of the outputs of the transmitting circuit.

3. A system according to claim 1, wherein the receiving circuit comprises an analog switch having an addressing input connected to the addressing bus and the same number of inputs as there are seals, a detector connected to the switch and a matching circuit connected to the detector.

4. A system according to claim 1, wherein the sampler comprises:
a rapid comparator with a positive input receiving the signal to be sampled and a negative input, a sampling control input and an output;
a counter having an input connected to the output of the comparator and a digital output;
a digital-analog converter having a digital input connected to the output of the counter and an analog output;
a current-voltage converter having an input connected to the output of the converter and an output connected to the negative input of the comparator;
a buffer memory having an input connected to the output of the counter and an output connected to a measurement data bus.

* * * * *